(12) United States Patent
Berberoglu et al.

(10) Patent No.: US 10,072,239 B1
(45) Date of Patent: Sep. 11, 2018

(54) MICROORGANISM CULTIVATION PLATFORM FOR HUMAN LIFE SUPPORT

(71) Applicants: The United States of America, as Represented by the Administrator of the National Aeronautics & Space Administration (NASA), Washington, DC (US); The Board of Regents of the University of Texas, Austin, TX (US)

(72) Inventors: Halil Berberoglu, Austin, TX (US); Thomas E. Murphy, Austin, TX (US); Leslie E. Bebout, Santa Cruz, CA (US); Erich D. Fleming, Redwood City, CA (US)

(73) Assignee: The United States of America as Represented by the Administrator of the NASA, Washington, DC (US)

( * ) Notice: Subject to any disclaimer, the term of this patent is extended or adjusted under 35 U.S.C. 154(b) by 771 days.

(21) Appl. No.: 13/929,646

(22) Filed: Jun. 27, 2013

Related U.S. Application Data (60) Provisional application No. 61/772,654, filed on Mar. 5, 2013.

(51) Int. Cl.
*C12M 1/107* (2006.01)

(52) U.S. Cl.
CPC ................... *C12M 21/04* (2013.01)

(58) Field of Classification Search
CPC ...... C12M 29/16; C12M 25/10; C12M 29/10; C12M 29/12; C12M 29/04; C12M 23/24; C12M 23/34; C12M 41/00; C12M 23/06; C12M 21/02; C12M 31/10; C12M 31/02;
(Continued)

(56) References Cited

U.S. PATENT DOCUMENTS

| | | | | |
|---|---|---|---|---|
| 3,821,087 A | * | 6/1974 | Knazek | C12M 25/10 435/297.4 |
| 5,005,787 A | | 4/1991 | Cullingford | |

(Continued)

OTHER PUBLICATIONS

Berberoglu, et al., Growth, CO2 consumption and H2 production of Anabaena variabilis ATCC 29413-U under different irradiances and CO2 concentrations, Journal of Applied Microbiology, 2008, 105-121, 104, 2007. The Authors.
(Continued)

*Primary Examiner* — Willaim H Beisner
*Assistant Examiner* — Danielle B Henkel
(74) *Attorney, Agent, or Firm* — Christopher J. Menke; Robert M. Padilla; Mark P. Dvorscak (57) ABSTRACT

A life support system for providing a growth medium for at least one photosynthetic micro-organism and for converting $CO_2$ to $O_2$, with reduced water use that is as low as about 4 percent of the corresponding amount of water normally required for conventional micro-organism growth. The system includes a liquid transport capillary channel, a mixed culture photosynthetic biofilm and a liquid transport substrate that is positioned between and contiguous to the capillary channel and the biofilm, where the liquid transport rate is adjustable by adjustment of the local humidity. Approximately uniform radiation is received by the biofilm and contributes to microorganism growth.

18 Claims, 10 Drawing Sheets

(58) Field of Classification Search
CPC .................. C12M 31/08; C12M 21/04; A61M 2001/3489
See application file for complete search history.

(56) References Cited

U.S. PATENT DOCUMENTS

| | | | |
|---|---|---|---|
| 8,691,538 B1* | 4/2014 | Moll | C12N 1/12 435/139 |
| 9,200,244 B2* | 12/2015 | Ehwald | C12M 21/02 |
| 2005/0081552 A1* | 4/2005 | Nilson | F28D 15/043 62/311 |
| 2010/0112723 A1* | 5/2010 | Battrell | B01L 3/502776 436/501 |

OTHER PUBLICATIONS

Raatschen, et al., Potential and Benefits of Closed Loop ECLS System on the ISS, Acia Astronautica, 2001, 411-419, 48-5-12, Elsevier Science Ltd, Great Britain.

\* cited by examiner

*Time zero photograph taken from a different rib

FIG. 7B time zero after 236 hours

MICROORGANISM CULTIVATION PLATFORM FOR HUMAN LIFE SUPPORT

ORIGIN OF THE INVENTION

The invention described herein was made, in part, in the performance of work under a NASA contract and by an employee of the United States Government and is subject to the provisions of Public Law 96-517 (35 U.S.C. § 202) and may be manufactured and used by or for the Government for governmental purposes without the payment of any royalties thereon or therefore.

FIELD OF THE INVENTION

This invention relates to a life support system that converts $CO_2$ and produces $O_2$.

BACKGROUND OF THE INVENTION

Long term support of humans in space currently depends on transport of consumables from Earth, with the International Space Station (ISS) being the primary example. Aboard the ISS, oxygen for human respiration is generated by purifying water and then splitting water into oxygen and hydrogen by electrolysis [ref 1]. Meanwhile, carbon dioxide produced by human respiration is scrubbed from the cabin air, concentrated, and emitted from the shuttle [2,3]. Furthermore, food is uploaded from Earth and solid waste is not reused. Therefore, current life support for humans in space depends on open loop technology, which in turn relies on access to supplies from Earth. This open loop technology requires periodic uploads and limits mission duration. Long term human-occupied missions must therefore seek closed loop life support.

The Micro-Ecological Life Support System Alternative (MELiSSA) project, initiated by the European Space Agency in 1989, aims to engineer a closed loop system consisting of five microbial compartments to completely recycle carbon, hydrogen, oxygen, nitrogen, sulfur, and phosphorous between the compartments and the human-occupied cabin. In addition, a subproject of MELiSSA, named BIORAT, aimed to use a centrifugal planktonic photobioreactor (PBR) to consume $CO_2$ and generate $O_2$ for a simulated human crew of two mice. The 5.6 L photobioreactor successfully supported the two mice for the entire testing period of three weeks [4]. However, the microorganisms in the BIORAT system were cultivated in a liquid medium with a dry weight density on the order of 1 g/L; roughly one kilogram of water is needed to cultivate one gram of biochemically active biomass. The water use intensity of such a system is a potential problem for space exploration where mass is an important constraint. The power consumption of a centrifugal reactor is also a concern. Current Life Support Technology Aboard the International Space Station.

The oxygen-generating system (OGS) currently aboard the ISS uses electrolysis to split water into hydrogen and oxygen [1,5]. The oxygen is vented into the cabin atmosphere. Some of the hydrogen is used in a Sabatier system to generate water and the rest is released into space. The OGS has a mass of 360 kg and is able to supply oxygen to the astronauts at a variable rate between 2.3 and 9.2 kg/day. The nominal oxygen generation rate is 5.4 kg/day, which is sufficient to support the maximum crew size of six. Moreover, the OGS requires approximately 3.6 kW of electric power, in addition to the 0.8 kW of electric power required to run the urine processing assembly and water processing assembly in series prior to the OGS [5]. Finally, oxygen generation aboard the ISS for a crew of six requires 1480 kg of water to be uploaded to space station from Earth annually [6].

A human exhales approximately 1 kg of carbon dioxide per day, and this $CO_2$ must be constantly removed from the cabin to avoid $CO_2$ toxicity [7]. The current solution to this problem is to first concentrate the exhaled $CO_2$ in a carbon dioxide concentrating assembly (CCA) [3,6]. The CCA consists of a zeolite molecular sieve that preferentially adsorbs $CO_2$. A blower is used to move air through the CCA at an approximate rate of 40 kg/hr. Once concentrated, the carbon dioxide follows one of two paths. Approximately 0.5 kg of each kilogram of concentrated $CO_2$ is fed into a Sabatier reactor. The Sabatier reactor, operated at approximately 225° C., uses a nickel catalyst to enable the reaction [8]

$$CO_2 + 4H_2 \leftrightarrow CH_4 + 2H_2O + \text{heat} \qquad (1)$$

The water from the reaction can be reinserted into the OGS or used for hygienic or cooking purposes, whereas the methane ($CH_4$) is presently vented to space. The zeolite material containing the other half of the $CO_2$ generated in the cabin is heated with electrical heaters to release the $CO_2$, which is emitted into space. The zeolite can then be reused. For normal operation at a crew size of six, the carbon dioxide removal system (CDRA) consumes approximately 840 W of electric power [9]. The CDRA system has a mass of approximately 200 kg.

There are currently no biological food generation capabilities aboard the ISS. Food is uploaded from Earth at an approximate rate of 1200 kg/year [7]. Closed-loop food production in human-occupied space missions must utilize a biological system. Many microorganisms, such as *Spirulina platensis*, and *Spirulina maxima* are currently commercially sold as food products and are good candidates for space food production. In addition to food production, a vast array of microbes can be used for remediating waste air and water streams using significantly less energy and mass than conventional space life support systems.

Figure 1:
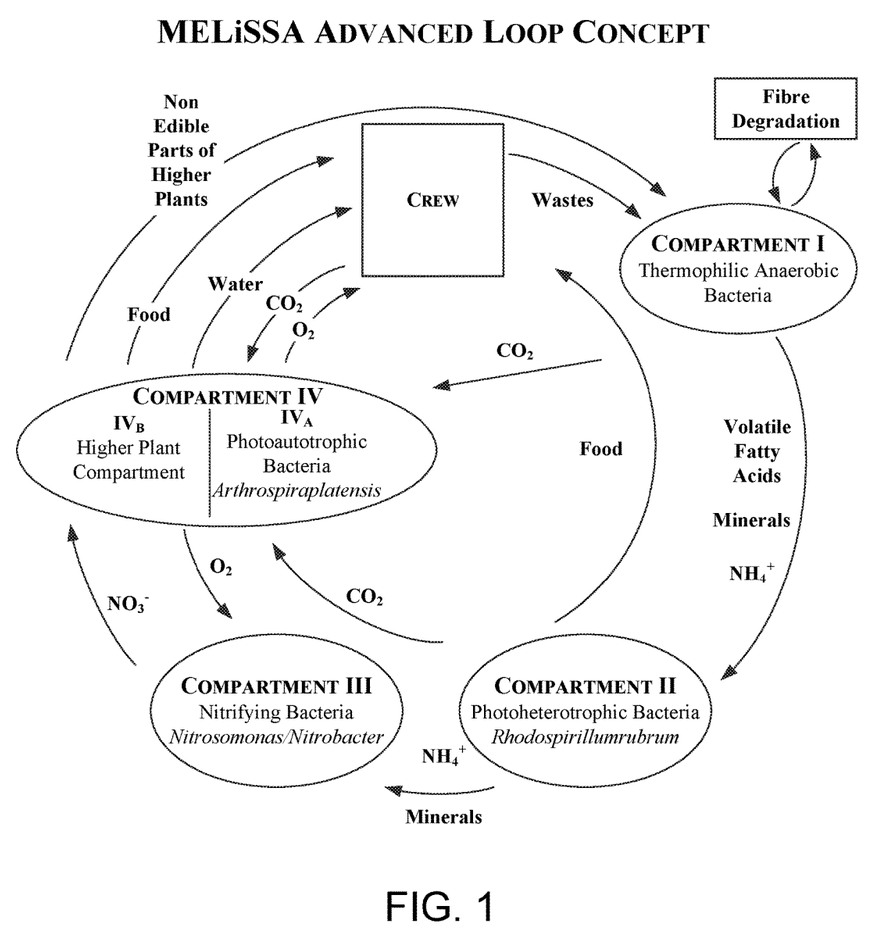
FIG. 1 illustrates the components of the MELiSSA project.

In 1989, the European Space Agency (ESA) initiated the Micro-Ecological Life Support System Alternative (MELiSSA) project [10-13]. The concept of the MELiSSA project is to construct an ecosystem that complements human metabolic processes in order to form a closed loop of the essential elements carbon, nitrogen, oxygen, and hydrogen. To do this, the system includes five compartments, each of which contains a distinct combination of microorganisms capable of specific metabolic pathways. FIG. 1 shows a schematic of the function and proposed microorganism concentration of each of the compartments.

Performance of an interconnected loop (Compartments III and IVa) has been demonstrated at the pilot facility scale [10]. Compartment III included a packed bed biofilm reactor with a total volume of 8 L and containing a co culture of *Nitrosomonas europaea* and *Nitrobacter winogradskyi*, which converted ammonium into nitrite and nitrite into nitrate, respectively. Compartment IVa included a 77 L gas-lift photobioreactor containing a planktonic culture of the green algae *Spirulina platensis*. The authors showed that at a flow rate of 14.5 l/day and an inlet ammonium concentration of 600 mg/l, Compartment III generated nitrate from ammonium at a rate of approximately 8 g/day. Data on the rate of $CO_2$ consumption by Compartment IV was not reported. It should be noted that a gas-lift photobioreactor depends on buoyancy to drive gas bubbles upward through the liquid phase, and this buoyant force does not exist in a microgravity environment. The current goal of the MELiSSA pilot facility is to demonstrate a complete nutrient recycling loop consisting of all five compartments by the year 2015 [14].

BIORAT is a subproject of MELiSSA that integrates Compartments IVa and V (photosynthetic bacteria and crew, respectively) to consume $CO_2$ and to generate $O_2$ for the crew [4].

For breadboard scale demonstration of Compartment Va, Denney et al [4] built a rotating annular photobioreactor that used centrifugal forces for gas exchange and liquid mixing. The reactor is essentially a gas lift reactor that uses centrifugal forces as a substitute for gravity. The photobioreactor was used to cultivate the cyanobacteria *Arthospira platensis*. The reactor measured 18 cm in diameter and 22 cm in length, for a total working volume of 5.6 L. The crew compartment was simulated by an 11.5 L air tight cage containing a mouse. Food and water were supplied to the mouse and liquid and solid waste were removed as needed and not resupplied.

A control system was implemented to control the rate at which the photobioreactor produced $O_2$ by varying the irradiance incident onto the photobioreactor. The workers operated the BIORAT system for 11 days with a constant oxygen volume fraction in the crew compartment of 0.21, by illuminating the photobioreactor with an irradiance of approximately 20 Watts/m². The maximum oxygen generation rate of the photobioreactor, tested independently of the crew compartment, was 409 mg $O_2$/hr at an incident irradiance of 115 Watts/m². At this maximum oxygen generation rate, it would require a photobioreactor volume of approximately 475 L to support one human. The results of this study were reported in the year 2000 and may be the last publication to date on the project.

$CO_2/O_2$ Exchange Using a Terrestrial Photobioreactor.

González López et al. engineered and operated a gas-lift photobioreactor containing *Anabaena* sp. for $CO_2$ consumption [15]. They reported a maximum experimental $CO_2$ consumption rate of 1.45 g $CO_2$ per liter of photobioreactor volume per day at a microorganism concentration of 1 g/L. At this rate, it would require approximately 0.7 kg of biochemically active biomass to support one human. At a biomass concentration of 1 g/l, which is typical of dense planktonic cultures, support of one human would require a planktonic culture volume and mass of approximately 700 L and 700 kg, respectively. Furthermore, because a gas-lift bioreactor cannot function in the absence of gravity, a mechanism similar to the centrifugal pump of the BIORAT photobioreactor would need to be integrated into such a photobioreactor to function in microgravity environments, further increasing the mass of the system.

Ideally, a life support system should process and reuse close to 100 percent of the consumables, especially water, should provide some conversion of $CO_2$ and production of $O_2$, and should use a small amount of power for such purpose. The reprocessing device(s) should have a small footprint, and the reprocessing should occur spontaneously and continuously.

In light of this challenge, we designed and prototyped a novel Surface-Adhering Bioreactor (SABR) in which microorganisms grow in densely packed biofilms (benthic) on a hydrophilic porous substrate rather than in suspension (planktonic). Furthermore, nutrient medium is passively delivered to the biofilm by evaporation and capillary forces. This makes gas and nutrient delivery independent of inertial and gravitational forces, as opposed to the centrifugal air lift photobioreactor component of the BIORAT system. As a proof of concept, we have prototyped a scaled-down SABR prototype to cultivate the cyanobacteria *Anabaena variabilis* and measure its rate of carbon dioxide consumption. At the same time, we prototyped a conventional photobioreactor of same size and active microorganism loading to evaluate the performance of SABR against the state-of-the-art planktonic PBRs. Finally, we identified ways to improve SABR performance and explored further uses of the SABR system.

SUMMARY OF THE INVENTION

The invention provides a life support system with the following interacting components: (1) a liquid transport capillary with a channel width that optionally decreases in moving between a first channel end and a second channel end, with a channel width preferably no more than about 2 mm; (2) a mixed culture photosynthetic biofilm, containing at least one photosynthetic micro-organism and spaced apart from the channel; (3) a porous, hydrophilic substrate, positioned between and contiguous to the channel on one side thereof and to the biofilm on a second side thereof; (4) where the substrate transmits a portion of liquid moving in the channel from a first substrate surface across the substrate toward a second substrate surface at a liquid transport rate that is adjustable; (5) where the biofilm has an exposed surface that receives radiation from a radiation source and also receives at least one of $CO_2$ and another gas species for the micro-organism; and (6) where the biofilm receives the liquid, the $CO_2$ and the at least one nutrient and promotes or supports growth of at least one photosynthetic micro-organism.

Optionally, transport of liquid in the capillary channel is partly by evaporation of liquid from the biofilm. This evaporation may result in accumulation of salt in or on the biofilm, and the invention optionally provides a selected terminal porous substrate that does not support microorganism growth in contact with the porous substrate. The invention also provides humidity control adjacent to the biofilm, optionally by providing an adjustment of liquid transport rate.

DESCRIPTION OF THE INVENTION

In long term space exploration missions, mass minimization of life support systems will be a primary engineering challenge. Furthermore, photobioreactors for use in life support systems will require nutrient and gas exchange mechanisms that are independent of gravitational forces. In light of these challenges, we engineered a Surface-Adhering Bioreactor (SABR) for microorganism cultivation at dry biomass densities of about 100 g DW/L. Fluid transport within the SABR system is accomplished with capillary forces and evaporation rather than by inertial forces. This technology enables significant mass and energy savings compared to the centrifugal gas-lift technology used in the BIORAT photobioreactor.

Figures 2A, 2B:
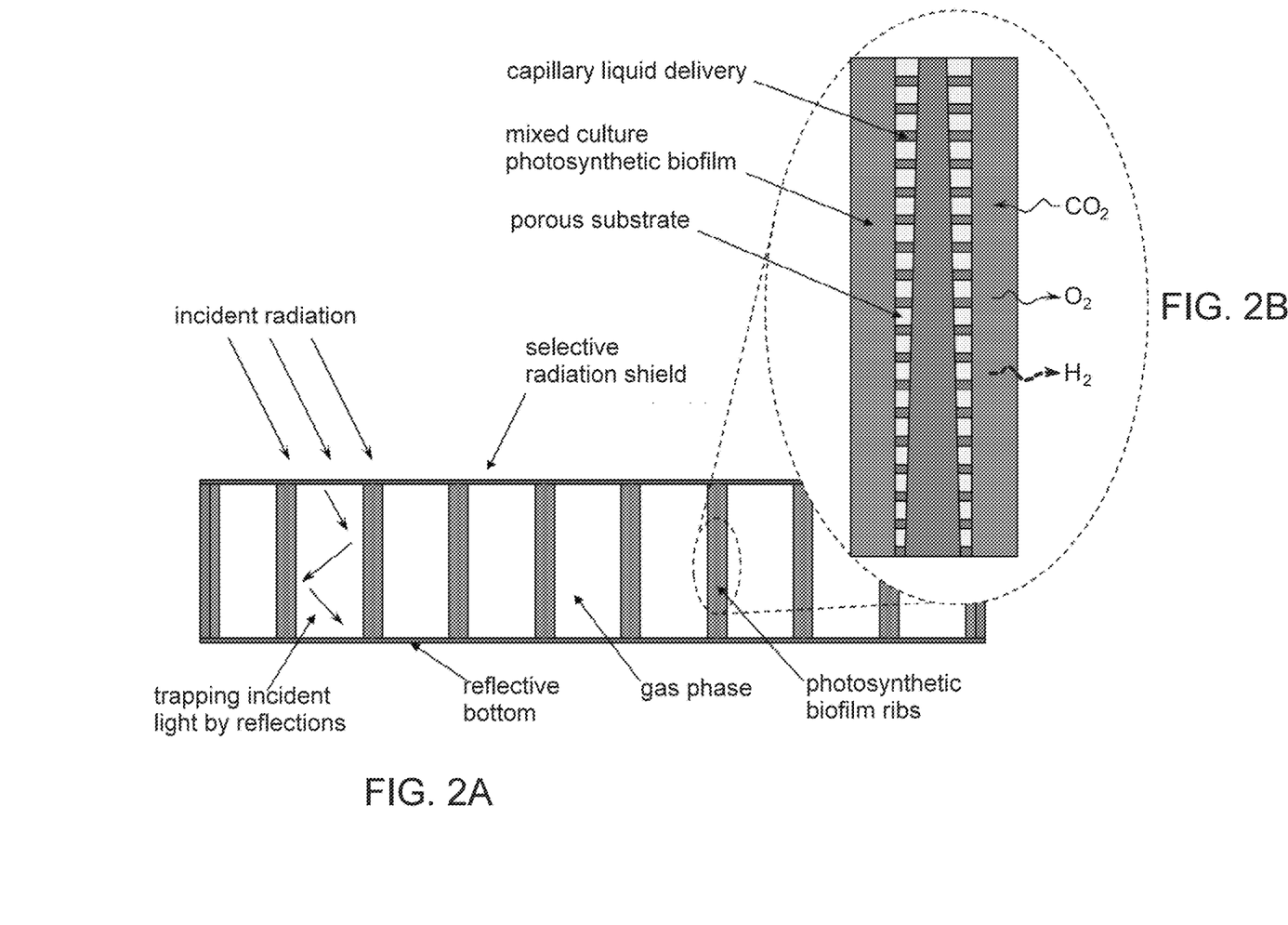
FIGS. 2A and 2B schematically illustrate of the SABR system, according to an embodiment of the invention.

FIGS. 2A and 2B show a schematic of the SABR system. Microorganisms are cultivated as a film on a hydrophilic, porous surface. Evaporation from the surface pulls fresh nutrient medium toward the biofilm. FIG. 2 shows an exemplary photosynthetic biofilm, in which the organisms use solar energy to convert atmospheric carbon dioxide and water to biomass, while producing oxygen, although the SABR platform can be used to cultivate a plethora of microorganisms for a variety of purposes, including but not limited to nitrogen fixation, hydrogen generation, production of nutraceuticals or other raw materials (for example, bioplastics) and organic matter degradation.

The system, shown in FIGS. 2A and 2B, includes a liquid transport channel, preferably with capillary liquid delivery, spaced apart from a mixed culture, photosynthetic biofilm by a supporting structure that is porous and hydrophilic. A porous substrate is positioned between and contiguous to the liquid channel and the biofilm, to deliver liquid and nutrients to the biofilm. The biofilm receives and absorbs $CO_2$ for microorganism growth and issues $O_2$ and $H_2$. The biofilm structure may be one, two or more spaced apart ribs that define a sequence of microorganism growth chambers that each receive incident radiation from a sun or from another light source. Some of the incident radiation is partly absorbed by the microorganisms and is partly reflected from a reflecting bottom or boom.

Figure 3A:
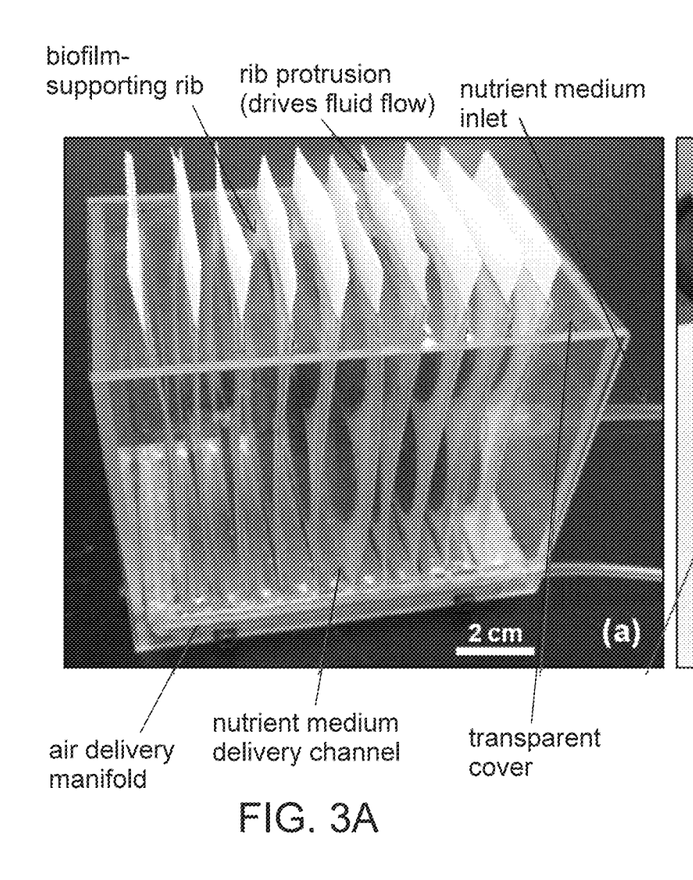
FIGS. 3A and 3B photographically illustrates a prototype of the invention and a prototype of a conventional planar photobioreactor, respectively.

We constructed a scaled down prototype of the SABR system that is 10 cm long, 6.5 cm wide, and 10 cm tall. FIG. 3A shows a photograph of the prototype that consists of 10 vertical ribs that support microorganism growth. The ribs are hydrophilic porous substrates of thickness 320 μm, made of cellulose with porosity 0.46 and average channel diameter 2 μm that measure 9.6 cm in height and 4.8 cm in width. The cyanobacteria Anabaena variabilis was used in the prototype due to its ability to fix nitrogen and high $CO_2$ consumption rate of 1.45 g $CO_2$/g biomass-day [15]. A 1 cm long section of each rib that does not support biofilm growth protrudes from the top of the device and acts as a driver for nutrient medium flow up the rib as the liquid evaporates from this section. The base of each rib rests in a 1.5 mm hydraulic diameter channel at the bottom of the device which contains fresh nutrient medium. Upward motion of nutrient medium through the rib feeds the biofilm, which grows on the rib's surface. As nutrient medium is consumed (nutrients and some water transfer to cells; remaining water evaporates), fresh nutrient medium is pulled through the inlet in the device's base. Air with carbon dioxide is delivered into the device through the manifold on the side.

Figure 3B:
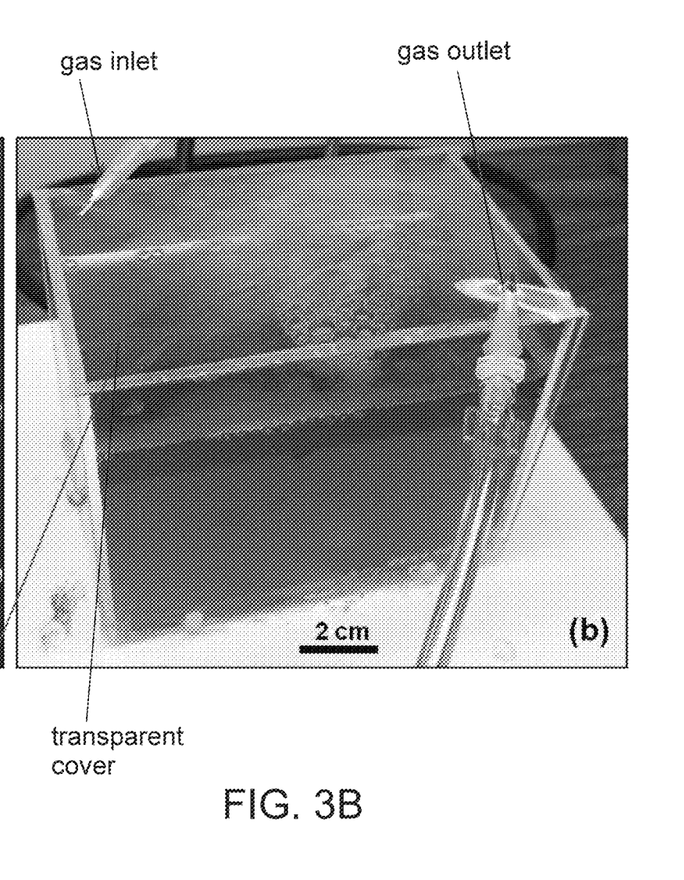

To compare the biomass productivity, working water mass, and system mass of the SABR prototype to those qualities of conventional photobioreactors, we also constructed a prototype of a planar photobioreactor with same dimensions as the SABR prototype, shown in FIG. 3B. To appropriately compare the two systems, we inoculated each system with the same amount of biochemically active biomass. We inoculated the conventional photobioreactor prototype (CPP) with 117 ml of Anabaena. variabilis culture in BG11 medium at a dry biomass concentration of 0.34 g/l. We filled the remainder of the CPP with 283 ml of fresh BG11 medium, for a total suspension volume of 400 ml at a dry biomass concentration of 0.1 g/l. We inoculated the SABR prototype by filtering Anabaena. variabilis culture from the same batch onto the ribs. Each side of the rib was inoculated with two 35 mm diameter circles, each containing 1 mg of biochemically active biomass. Thus, each prototype initially contained 40 mg of biochemically active biomass. The masses of the SABR prototype and the CPP prototype are 215 g and 561 g, respectively. The water masses of the SABR prototype and the CPP prototype are 16 g and 400 g, respectively. Thus, SABR offered a reduction of 96 percent in water mass and 62 percent in overall system mass, relative to the CPP.

A magnetic stir bar was inserted into the CPP for adequate mixing. Each prototype was placed under a cool, white fluorescent light bulb, and the incident irradiance onto the top horizontal surface of each prototype was approximately 130 Watts/m$^2$. Air with 0.8 percent $CO_2$ by volume was pumped through the manifold of the SABR prototype and into the headspace of the CPP prototype at a flow rate of 35 ml/min. For initial testing, we have monitored the biomass productivity of each prototype by periodically monitoring the chlorophyll content of each prototype over time.

Figure 4A:
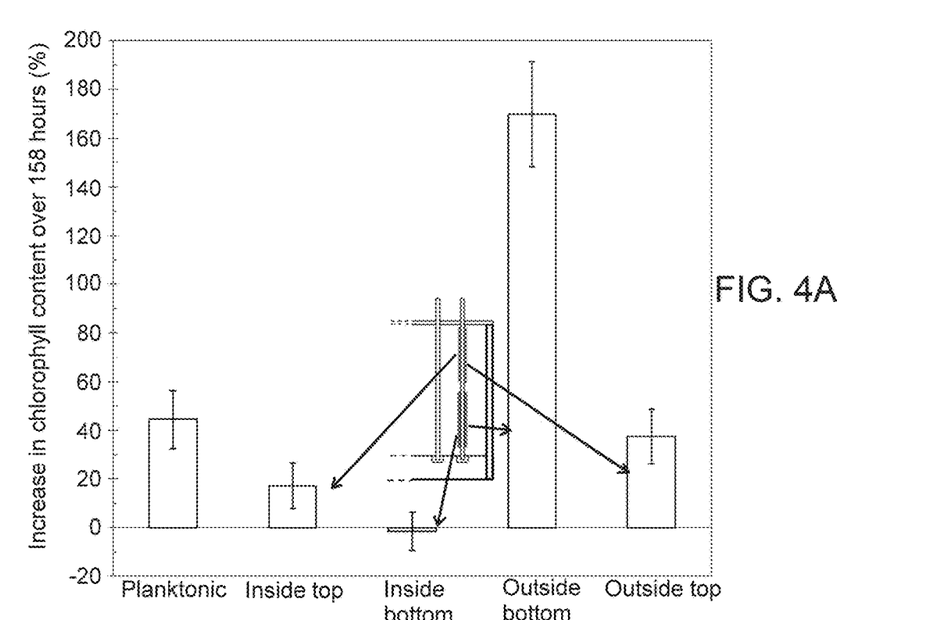
FIGS. 4A and 4B graphically illustrate chlorophyll content in a CPP system and in a SABR system.
Figure 4B:
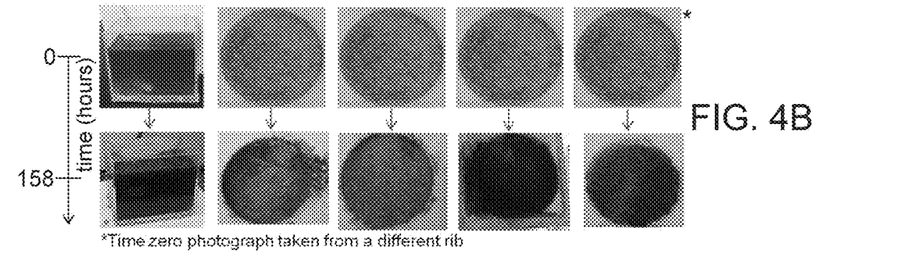

FIG. 4A graphically illustrates increase in chlorophyll content in a CPP and in a SABR system at the end of 158 hours of operation of each system. FIG. 4B photographically indicates that a bottom section of an out-facing rib of a SABR showed a 400 percent increase in productivity, compared with the CPP productivity. However, at all other sections, the increase in productivity of SABR relative to CPP was lower.

FIG. 4B also displays images of freshly inoculated SABR and CPP systems at an initial time (t=0) and at the end of the experiment (t=158 hrs). The grey scale intensities of these images correlated well with the chlorophyll extraction results obtained. We believe that nutrient limitation was the principal reason for the greater productivity of the bottom sample(s) compared to the top sample(s). Because the nutrient medium was fed from the bottom and directed toward the top, nutrients were partly consumed as the nutrient medium flowed upward toward the top of the rib, and the medium at the top was less nutrient-rich than the medium at the bottom. This nutrient limitation can be mitigated with a strategic flow network that delivers nutrient to the top-most and bottom-most regions in parallel, rather than in series.

We further believe that light limitation was a principal reason for the greater productivity associated with the bottom regions. A rib adjacent to the rib we tested was not perfectly vertical. Rather, the adjacent rib bowed slightly and thus prevented a portion of the light from reaching the bottom region of the rib we tested.

Testing a Single SABR Rib Prototype.

Figure 5:
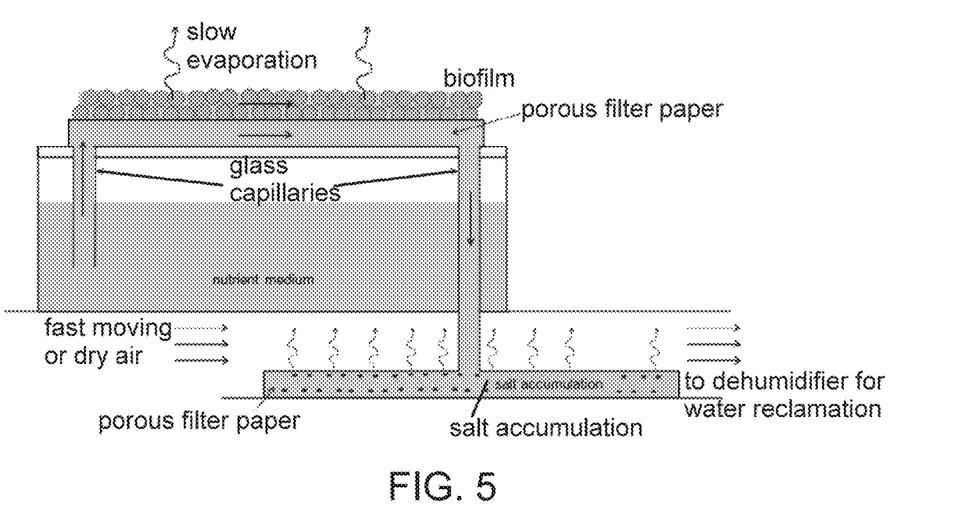
FIG. 5 illustrates a system for mitigation of salt build-up.

We designed a single rib SABR prototype and a test chamber for measuring the rates of gas exchange by the biofilm. The biofilm grows on a porous, hydrophilic medium that is fed nutrient medium from below via a glass capillary in contact with a reservoir. One challenge we faced in the initial design was that water evaporation from the surface caused salt accumulation in the biofilm. In light of this challenge, we modified the setup to include an exit capillary from the biofilm-supporting porous medium in contact with a terminal porous medium that collects the salts. Dry air is in contact with the terminal filter paper to induce a flow of liquid toward it. FIG. 5 schematically illustrates the salt buildup mitigation concept. Additionally, the terminal porous substrate can be placed in direct contact with the porous substrate that supports biofilm growth, rather than being supported by a capillary.

Figure 6:
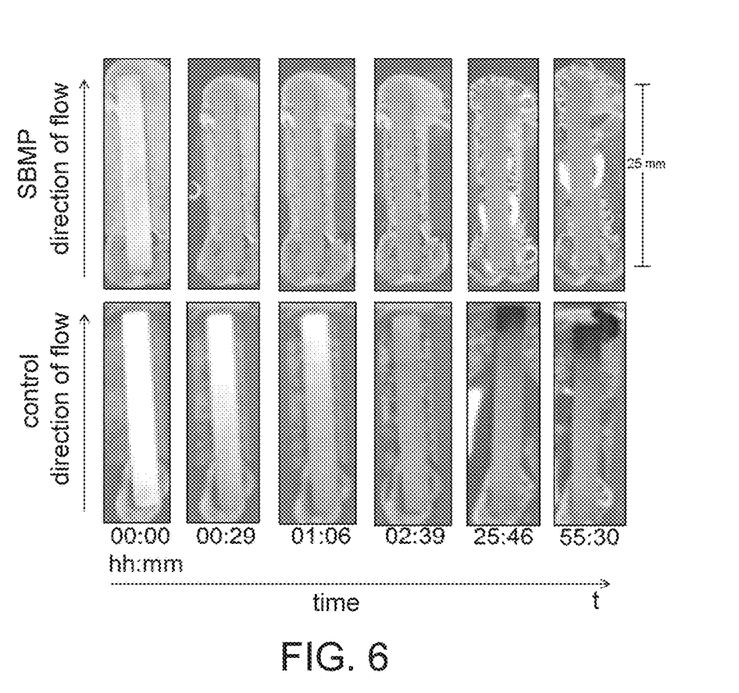
FIG. 6 illustrates mitigation of salt build-up in a modified setup.

We made regions of salt accumulation visible in in the original single prototype design as well as the salt buildup mitigation by using water with red food coloring instead of nutrient medium. FIG. 6 shows photographs of the control setup and the salt buildup mitigation setup at various times after the introduction of red food coloring to the fluid reservoir.

As shown in FIG. 6, red food coloring accumulated in the control setup, but not in the salt buildup mitigation setup. Therefore, we designed our single rib prototypes to include the salt buildup mitigation technology.

Figure 7A:
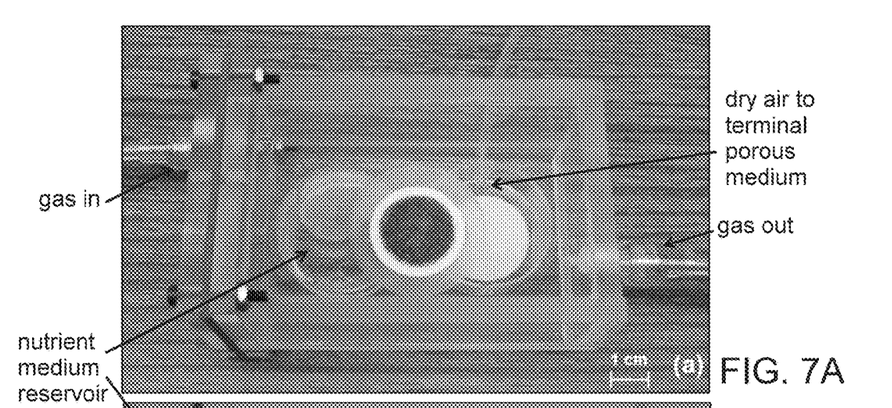
FIGS. 7A and 7B photographically illustrate a top view and a side view of a test chamber used to measure a rate of $CO_2$ consumption.
Figure 7B:
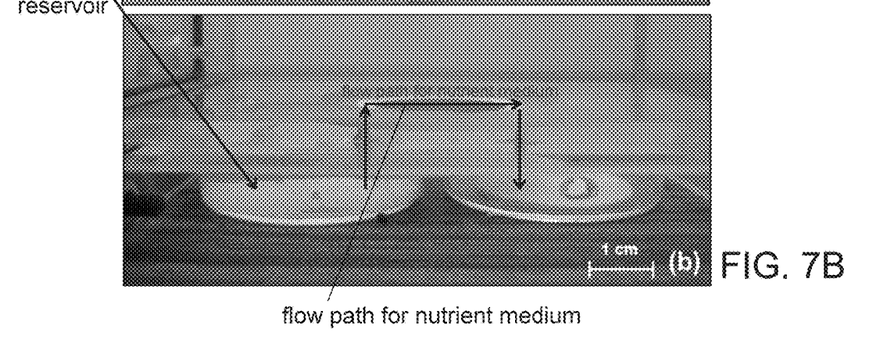

We constructed transparent, air-tight, acrylic test chambers to measure the rate of carbon dioxide consumption in the biofilm. FIGS. 7A and 7B show the test chamber containing an *Anabaena variabilis* biofilm on a 25 mm diameter filter paper. In FIG. 7A, air with $CO_2$ enters the chamber on the left and exits on the right. Dry air is delivered to the bottom chamber containing a terminal filter paper. As liquid evaporates from the terminal filter paper, fresh nutrient medium is pulled through the flow circuit, as shown in FIG. 7B.

Biofilm Growth in the Test Chamber.

Figure 8A:
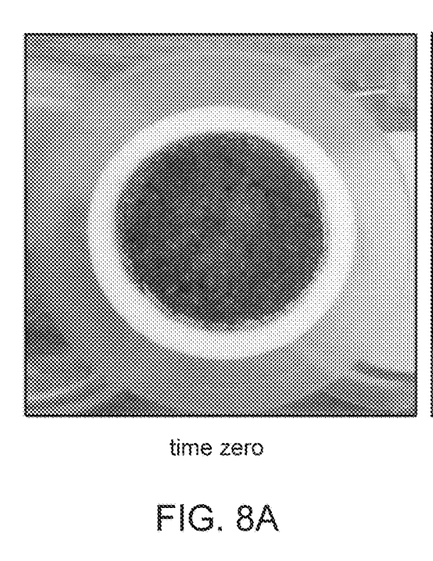
FIGS. 8A and 8B illustrate biofilm growth at time t=0 and t=236 hours, respectively.
Figure 8B:
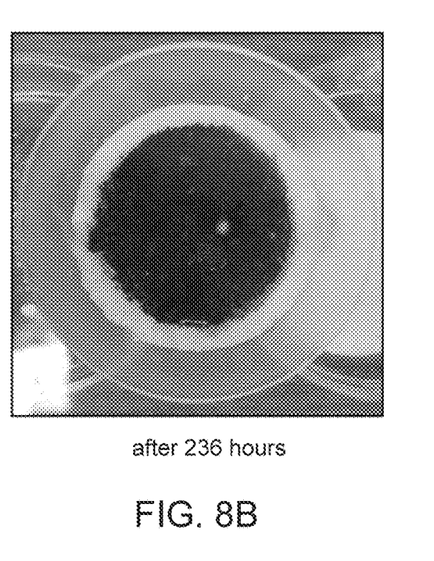

We inoculated a 17.5 mm diameter circle on the biofilm-supporting filter paper with 1 ml of *Anabaena variabilis* culture with a dry biomass concentration of 1.0 g/l for an initial areal biomass density of 0.42 mg/cm$^2$. BG11 was used as the nutrient medium. Air with an approximate $CO_2$ concentration of 0.2 percent was pumped into the chamber at an approximate rate of 30 ml/min over the course of 21 days. FIGS. 8A and 8B show the biofilm at the time of inoculation and after 236 hours of operation.

Single Rib $CO_2$ Consumption Data.

Figure 9:
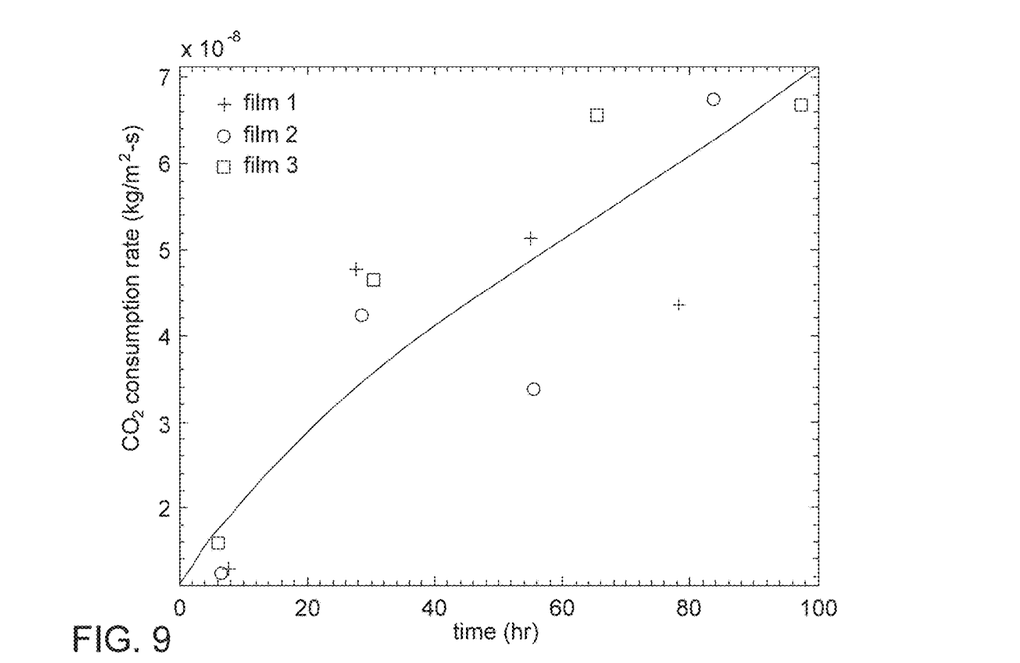
FIG. 9 graphically illustrates cumulative $CO_2$ consumption per unit area for three single rib prototypes for a time interval of about 100 hours.

The net photosynthetic $CO_2$ consumption rate was calculated as a product of the gas flow rate through the chamber and the difference in $CO_2$ concentration in the exit stream with the light source on and with the light source off. FIG. 9 shows the $CO_2$ consumption rate of the biofilm over a time interval of three weeks. FIG. 9 indicates that the $CO_2$ consumption rate declined from 5.4 mmol/m$^2$-hr at a biofilm lifetime of five days to 2.4 mmol/m$^2$-hr at a biofilm lifetime days. The reason for the decline in $CO_2$ consumption rate is a topic for ongoing research.

Potential Mass Savings Using SABR Instead of Planktonic Photobioreactors.

Due to the increased biomass density and enhanced biomass productivity of the organisms in SABR, the culture volume required to consume the $CO_2$ exhaled by one human is diminished by a factor of approximately 200, compared to planktonic systems. These results are summarized in Table 1.

TABLE 1

Biomass concentration and biomass productivity comparison between a single rib of SABR and two planktonic photobioreactors

|  | $CO_2$ consumption rate (mol $CO_2$/kg DW-hr) | Microorganism density (g/L) | Culture volume to support one human (L) |
|---|---|---|---|
| SABR extrapolation | 5.0 | 78 | 2.4 |
| BIORAT prototype | 2.0 | 1 | 475.0 |
| Gas-lift PBR | 1.4 | 1 | 678.6 |

As shown in Table 1, approximately 2.4 L of culture volume would be required to consume the $CO_2$ at the rate of exhalation by one human. At a biofilm thickness of 20 μm, approximately 120 m$^2$ of surface area would be required to fulfill this volume requirement. However, as shown in FIG. 2, the SABR design involves multiple ribs to act as a diffuser of incident radiation. If radiation is normally incident onto the top face of SABR (top as shown in FIG. 2), an appropriately aligned reflecting surface on the bottom boom can diffuse that irradiance uniformly onto the vertical biofilms. In this way, the irradiance incident onto each vertical biofilm is equal to $G_{in}/2N$, where $G_{in}$ is the irradiance incident onto the top face of SABR and N is the number of ribs per meter of SABR length. If N is 50 ribs/m and the incident irradiance is 1000 Watts/m$^2$, the irradiance incident onto each biofilm is 10 Watts/m$^2$, which is equal to the irradiance we used in our prototype testing. In this way, the biofilm area requirement of 120 m$^2$ can be satisfied by a SABR system with 50 ribs per meter of length and a length, width, and height of 1.2 m, 1 m, and 1 m, respectively. We estimated the mass of such a system by computing the total mass of the wetted ribs, the wet biomass, the housing structure, and the nutrient medium reservoir on the base plate. Our estimate of the system mass was 36 kg. By comparison, if the BIORAT prototype were scaled up to consume the $CO_2$ from one human, a culture mass of 475 kg would be required, and this mass does not include the mass of structural elements of the bioreactor.

Design Improvements to the SABR for Increased Productivity.

We outline some of the challenges in increasing the SABR's overall photosynthetic rate and propose solutions to these challenges.

Sluggish Nutrient Transport Through the Biofilm Environment.

Figure 10:
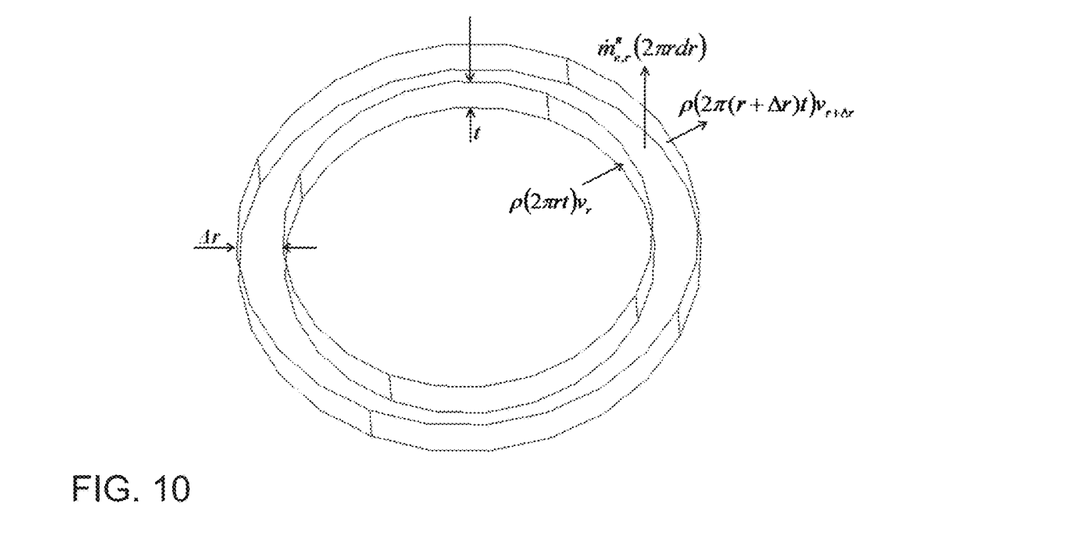
FIG. 10 illustrates a control volume used to determine local velocity of a nutrient medium through a porous medium.

The delivery rates of different nutrients in the cells in the biofilm can be limiting to growth, if these delivery rates are not balanced with the photon delivery rate. We performed a control volume analysis to determine the bulk nutrient medium velocity outward from the glass capillary source as a function of distance from the source and evaporative flux from the biofilm. FIG. 10 shows the control volume used for analysis and the mass flows through the volume.

Conservation of water mass requires that the water mass entering the control volume must either exit the control volume radially or exit from the system by evaporation:

$$\rho(2\pi r t)v_r = \rho(2\pi(r+\Delta r)t)v_{r+\Delta r} + \dot{m}''_e(2\pi r \Delta r) \qquad (2)$$

Solution of this equation for a circular porous medium with radius R and thickness t, subject to the boundary condition that the water is nonmoving at the outer edge, yields the water velocity field defined by:

$$v(r) = \frac{\dot{m}''_e R}{2\rho t}\left[\frac{R}{r} - \frac{r}{R}\right], \qquad (3)$$

where $\dot{m}''_e$ is the evaporative flux from the surface in kg/m²-s, $\rho$ is the density of water in kg/m³, and r is the local radius in m.

Figure 11:
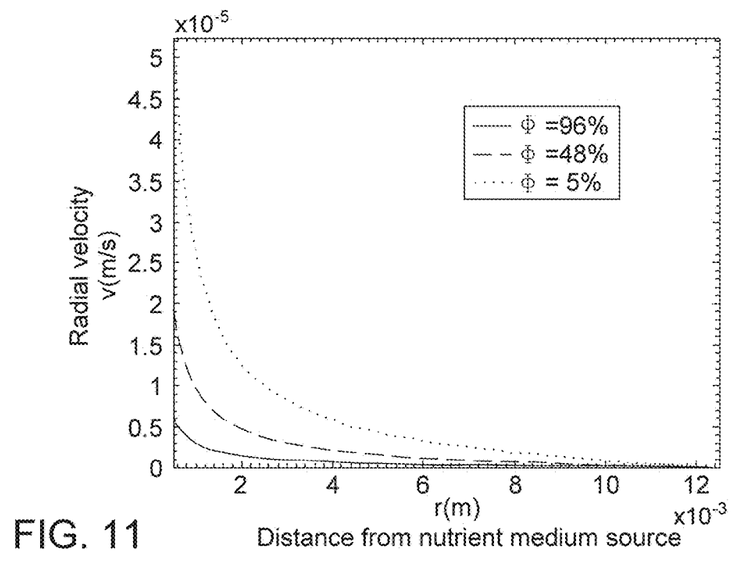
FIG. 11 graphically illustrates radial velocity of nutrient medium moving through a biofilm environment, as a function of distance from the nutrient medium inlet.

FIG. 11 shows the local radial water velocity as a function of local distance from the water source for three different surrounding relative humidity values. As shown in this figure, the nutrient medium velocity varies inversely with the relative humidity of the gas stream, because decreasing the humidity increases the rate of evaporation. This analysis holds for the optional terminal porous substrate used to drive flow through the biofilm.

Coupled with species diffusion models and models for microorganism consumption of nutrients, the flow rate through the system can be tuned to deliver nutrients at the rate at which the microorganisms can use them.

Limitation of Light Absorption in the Biofilm.

The biofilm used for the single rib SABR experiments was 5 μm thick and was irradiated with cool, white fluorescent bulbs at an irradiance of approximately 130 Watts/m². A single *Anabaena variabilis* cell is approximately cylindrical in shape, with an approximate length and diameter of 5 μm and 2.5 μm, respectively. Thus, the biofilm tested was more than one cell thick in many places. The maximum irradiance experienced by the cells was 130 Watts/m², but the irradiance below the top layer of cells is less than this value, due to absorption by the top layer. We are designing experiments to measure the photosynthetic rate of *Anabaena variabilis* as a function of irradiance. We are also developing biofilm light transfer models to predict the local irradiance in a photosynthetic biofilm as a function of depth and microorganism pigmentation. Coupled with mass diffusion models for nutrient and gas transport through the biofilm environment, the results of the aforementioned models and experiments will support design of optimum biofilm thickness and lighting conditions.

Figure 12:
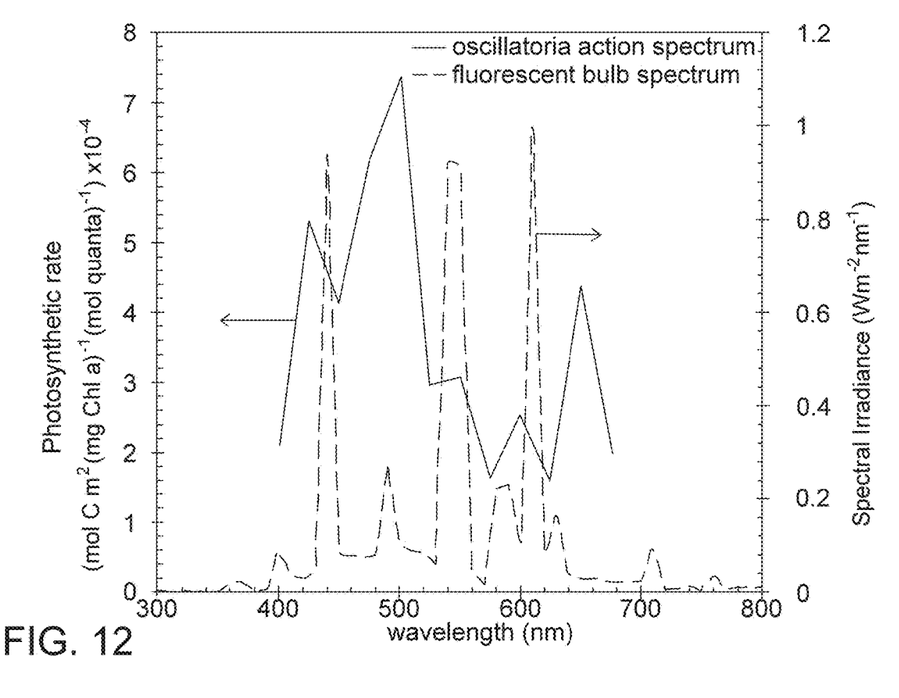
FIG. 12 graphically compares photosynthetic rate versus wavelength for a cyanobacterium, Oscillatoria, with emission spectrum for a cool, white fluorescent bulb.

Furthermore, fluorescent lamps are inefficient in providing light for cyanobacteria because their emission spectrum has peaks that do not coincide with the absorption peaks of cyanobacteria. Thus, much of the light provided by the lamps cannot be used for photosynthesis. FIG. 12 shows the emission spectrum of the fluorescent lamp we used in the experiments, together with the photosynthetic action spectrum for *Oscillatoria*, a genus of filamentous cyanobacteria similar to *Anabaena variabilis* [16,17]. The figure shows that the fluorescent bulb's emission peaks do not align with the peaks for the action spectra of *Oscillatoria*. We are developing efficient monochromatic LED light sources for enhanced photosynthetic efficiency.

Full-Scale Model: Bottom Reflective Boom Design for Optimal Light Transfer.

In future SABR designs, all of the incident collimated radiation will be diffused onto the top surface of the SABR system onto the biofilm surface uniformly. Coupled with appropriate rib spacing, optimum design of the bottom reflecting boom covering the channel network can control the amount of irradiance incident onto the biofilms.

It is assumed that collimated light enters the space between the ribs and that this collimated light is normal to the bottom reflecting boom. It is further assumed that the bottom reflecting boom is composed of specular mirrors; the angle that the collimated light beam makes with the line normal to the mirror is equal to the angle that the reflecting beam makes with the normal line.

Figure 13A:
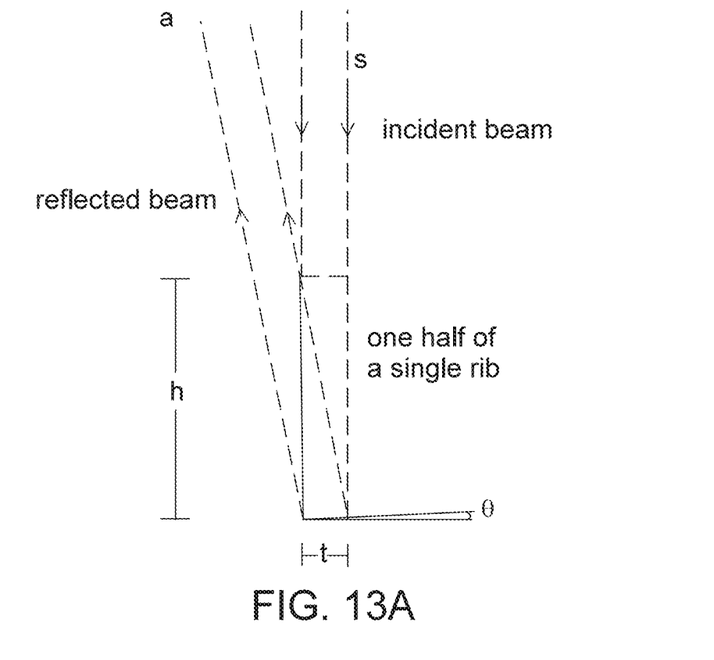
FIGS. 13A and 13B illustrate use of specular reflection for an incident beam in the SABR system.

FIG. 13A shows a vertical collimated beam reflecting off the bottom surface. One half of one rib is shown for simplicity with height h and width t. The system will be designed symmetrically about a line segment s in the Figure.

As shown, there is an angle $\theta$ that reflects the incident beam onto the vertical biofilm surface uniformly. Thus, the goal of the present analysis is to determine the angle $\theta$ which reflects the beam traveling along line s to the top corner of the vertical biofilm, corresponding to uniform illumination.

Figure 13B:
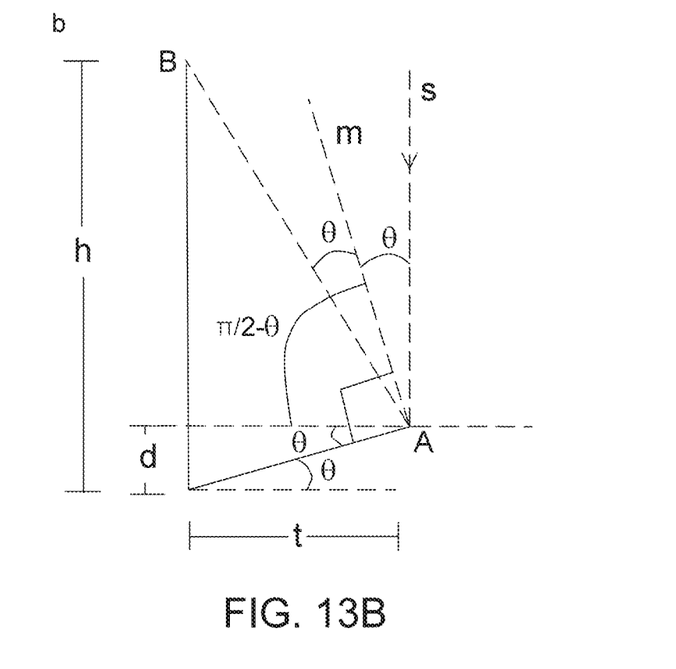

FIG. 13B shows an exploded view for ease of determination of this angle. In this Figure, the beam s is incident onto the mirror surface at A and is reflected to B. Upon inspection of the geometry, it can be shown that $$\tan\left(\frac{\pi}{2} - 2\theta\right) = \frac{h-d}{t} \tag{4}$$

where d is equal to t tan $\theta$. With this substitution, Equation (4) becomes $$\tan\left(\frac{\pi}{2} - 2\theta\right) = \frac{h}{t} - \tan\theta \tag{5}$$

Using a double angle relation, tan $2\theta = 2\tan\theta/(1-1\tan^2\theta)$, an exact solution of Eq. (5) is $$\tan\theta = \{1+(2h/t)\}^{-1/2}. \tag{6}$$

Thus, $\theta$ is dependent only on the aspect ratio h/t and varies inversely with this quantity. One can design the bottom reflecting boom in such a way that distributes light uniformly to the biofilm surfaces.

Future Applications of the SABR Platform.

Although a particular embodiment of the SABR system is shown in our experiments to support photosynthetic organism growth to assimilate $CO_2$, we are expanding the capabilities of this cultivation platform. We are investigating the feasibility of using a SABR platform to cultivate nitrogen fixing bacteria that convert ammonium to nitrite and nitrite to nitrate. We will design systems with multiple SABRs in series to form a closed nutrient loop. In this way, an interconnected biofilm ecosystem loop can be formed.

CONCLUSION

We constructed and operated a scaled-down photosynthetic surface adhering bioreactor (SABR) consisting of *Anabaena variabilis* for carbon dioxide consumption for long term human-occupied space mission. The results indicate that, in order to consume the carbon dioxide exhaled by a one human in a 24-hour period, 36 kg of system mass would be required at the $CO_2$ removal rate we measured. To consume the same amount of $CO_2$, the photobioreactor used in the BIORAT project would require 475 kg of culture mass, not including mass of the structural elements. Furthermore, the single rib system we designed was not optimized for maximum productivity, and we suggested some strategies to increase biofilm productivity.

REFERENCES

[1] T. Malik, "Air Apparent: New Oxygen Systems for the ISS," Space.com, 2006. [Online]. Available: http://www.space.com/2052-air-apparent-oxygen-systems-iss.html. [Accessed: 2011].

[2] W. Harwood, "Station's carbon dioxide scrubber back on line," CBS News "Space Place," 2009. [Online]. Available: http://spaceflightnow.com/shuttle/sts127/090726fd12/index.html. [Accessed: 2011].

[3] D. El Sherif and J. C. Knox, *International Space Station Carbon Dioxide Removal Assembly (ISS CDRA) Concepts and Advancements.* 2005, pp. 1-5.

[4] D. Demey, V. Hermans, J.-F. Cornet, J.-J. Leclercq, C. Lasseur, and A. Delahaye, "BIORAT: Preliminary evaluation of biological life support in space environment," in *30th International Conference of Environmental Systems,* 2000.

[5] R. M. Bagdigian and D. Cloud, *Status of the International Space Station Regenerative ECLSS Water Recovery and Oxygen Generation Systems.* 2005.

[6] W. Raatschen and H. Preiss, "Potential and benefits of closed loop ECLS systems on the ISS," *Acta Astronautica,* vol. 48, no. 5-12, pp. 411-419, 2001.

[7] V. N. Sychev, M. A. Levinskikh, and I. G. Podolsky, "Biological component of life support systems for a crew in long-duration space expeditions," *Acta Astronautica,* vol. 63, pp. 1119-1125, 2008.

[8] P. J. Lunde, "Modeling, Simulation, and Operation of a Sabatier Reactor," *Industrial and Engineering Chemistry Process Design and Development,* vol. 13, no. 3, pp. 226-233, 1974.

[9] Knox, J. Email correspondence. 27 Oct. 2011.

[10] F. Godia et al., "The MELISSA pilot plant facility as an integration test-bed for advanced life support systems," *Advances in Space Research,* vol. 34, pp. 1483-1493, 2004.

[11] L. Hendrickx et al., "Microbial ecology of the closed artificial ecosystem MELiSSA (Micro-Ecological Life Support System Alternative): Reinventing and compartmentalizing the Earth's food and oxygen regeneration system for long-haul space exploration missions," *Research in Microbiology,* vol. 157, pp. 77-86, 2006.

[12] F. Godia et al., "MELISSA: a loop of interconnected bioreactors to develop life support in Space," *Journal of Biotechnology,* vol. 99, pp. 319-330, 2002.

[13] B. Farges, L. Poughon, C. Creuly, J.-F. Cornet, C.-G. Dussap, and C. Lasseur, "Dynamic Aspects and Controllability of the MELiSSA Project: A Bioregenerative System to Provide Life Support in Space," *Applied biochemistry and biotechnology,* vol. 151, pp. 686-699, 2008.

[14] L. Poughon, B. Farges, C.-G. Dussap, F. Godia, and C. Lasseur, "Simulation of the MELiSSA closed loop system as a tool to define its integration strategy," *Advances in Space Research,* vol. 44, pp. 1392-1403, 2009.

[15] C. V. Gonzalez-Lopez, F. G. Acien Fernandez, J. M. Fernandez-Sevilla, J. F. Sanchez Fernandez, M. C. Ceron Garcia, and E. Molina Grima, "Utilization of the cyanobacteria *Anabaena* sp. ATCC 33047 in CO2 removal processes," *Bioresource Technology2,* vol. 100, pp. 5904-5910, 2009.

[16] M. R. Lewis, O. Ulloa, and T. Platt, "Photosynthetic action, absorption, and quantum yield spectra for a natural population of *Oscillatoria* in the North Atlantic," *Limnology and Oceanography,* vol. 33, no. 1, pp. 92-98, 1988.

[17] H. Berberoglu, H. Barra, L. Pilon, and J. Jay, "Growth, CO2 consumption, and H2 production of *Anabaena variabilis* ATCC 29413-U under different irradiances and CO2 concentrations," *Journal of Applied Microbiology,* vol. 104, pp. 105-121, 2008.

What is claimed is:

1. A life support system for converting carbon dioxide ($CO_2$) and producing oxygen ($O_2$), the system comprising:
   at least one section formed as a vertical strip, the at least one section having:
      at least one channel configured and arranged for receiving and transporting a liquid in a first direction, the channel decreasing in width along an entire length in a direction from a first channel end proximate a top of the vertical strip to a second channel end proximate a bottom of the vertical strip;
   a photosynthetic biofilm, the biofilm having an exposed surface;
   at least one photosynthetic microorganism in the biofilm; and
   a porous, hydrophilic substrate positioned between and contiguous to the biofilm and to the at least one channel, the substrate having pores configured for receiving liquid from the channel and redirecting the liquid in a second direction transverse to the first direction;
   wherein the liquid is passively moved from the channel, through the substrate, and through the biofilm by force arising from evaporation of liquid from at least one of the substrate and the exposed surface of the biofilm.

2. The life support system according to claim 1, wherein the at least one section further comprises a plurality of channels.

3. The life support system according to claim 2, further comprising at least one additional section positioned parallel to and spaced apart from the at least one section.

4. The life support system according to claim 1, wherein the photosynthetic microorganism is at least one of *Anabaena variabilis, Arthrospira platensis, Arthrospira maxima, Spirulina platensis, Spirulina maxima, Nitrosomas europaea, Nitrobacter winogradskyi, Anabaena,* and *Oscillatoria.*

5. The life support system according to claim 1, wherein an amount of liquid in the channel required to support growth of the at least one photosynthetic microorganism is no greater than about 4% of an amount of liquid that would be required to support growth of the at least one photosynthetic microorganism in a growth medium that does not require a force arising from evaporation of liquid for transport.

6. The life support system according to claim 1, wherein the at least one section further comprises an exit channel leading from the substrate to a terminal porous medium configured for collecting salt accumulated during evaporation of the liquid, the terminal porous medium not supportive of microorganism growth.

7. The life support system according to claim 1, wherein the at least one section further comprises a terminal porous medium in contact with the substrate configured for collecting salt accumulated during evaporation of the liquid, the terminal porous medium not supportive of microorganism growth.

8. The life support system according to claim 1, wherein the biofilm is positioned to receive radiation on the exposed surface from a radiation source, the radiation having an irradiance of at least 0.013 Watts/$cm^2$.

9. The life support system according to claim 8, wherein the biofilm is positioned to receive radiation reflected at least once from a reflecting surface.

10. The life support system according to claim 1, further comprising a humidity control mechanism positioned adjacent the biofilm.

11. The life support system according to claim 10, wherein the humidity control mechanism is positioned for adjusting rate of liquid transport by controlling humidity.

12. The life support system according to claim 10, wherein the humidity control mechanism is positioned for controlling a rate of delivery of liquid by controlling humidity.

13. A life support system for converting carbon dioxide (CO2) and producing oxygen ($O_2$), the system comprising:
- a plurality of sections formed as a plurality of strips, each strip having:
  - a plurality of channels configured and arranged for receiving and transporting a liquid in a first direction, each channel of the plurality of channels decreasing in width along an entire length in a direction from a first channel end proximate a top of the strip to a second channel end proximate a bottom of the strip;
  - a photosynthetic biofilm, the biofilm having an exposed surface;
  - at least one photosynthetic microorganism in the biofilm; and
  - a porous, hydrophilic substrate positioned between and contiguous to the biofilm and to the plurality of channels, the substrate having pores configured for receiving liquid from the plurality of channels and redirecting the liquid in a second direction transverse to the first direction;
  - wherein the liquid is passively moved from the plurality of channels, through the substrate, and through the biofilm by force arising from evaporation of liquid from at least one of the substrate and the exposed surface of the biofilm,
  - wherein the plurality of strips are positioned within a chamber substantially perpendicular to a reflective bottom surface of the chamber, each strip of the plurality of strips parallel to and spaced apart from an adjacent strip.

14. The life support system according to claim 13, wherein each of the plurality of strips has an end protruding from the chamber past top edges of the four side walls, the end configured to drive liquid flow up the strip.

15. The life support system according to claim 13, wherein the biofilm is positioned to receive radiation reflected from the reflective bottom surface of the chamber.

16. The life support system according to claim 13, wherein each of the plurality of strips comprises an exit channel leading from the substrate to a terminal porous medium configured for collecting salt accumulated from the liquid during evaporation.

17. The life support system according to claim 13, wherein each of the plurality of strips comprises a terminal porous medium in contact with the substrate configured for collecting salt accumulated from the liquid during evaporation.

18. A method for cultivating photosynthetic microorganisms, the method comprising:
- providing the life support system according to claim 1;
- inoculating the biofilm with the at least one photosynthetic microorganism;
- adding the liquid to the life support system, the liquid a nutrient medium;
- supplying air including carbon dioxide ($CO_2$) to the life support system;
- providing radiation from a radiation source to the life support system; and
- growing the at least one photosynthetic microorganism on the biofilm to cultivate the photosynthetic microorganisms.

* * * * *